United States Patent [19]

Dubeck et al.

[11] Patent Number: 4,476,331

[45] Date of Patent: Oct. 9, 1984

[54] TWO STAGE HYDROGENOLYSIS OF CARBOHYDRATE TO GLYCOLS USING SULFIDE MODIFIED RUTHENIUM CATALYST IN SECOND STAGE

[75] Inventors: Michael Dubeck, Birmingham; Gordon G. Knapp, Southfield, both of Mich.

[73] Assignee: Ethyl Corporation, Richmond, Va.

[21] Appl. No.: 529,727

[22] Filed: Sep. 6, 1983

Related U.S. Application Data

[62] Division of Ser. No. 348,026, Feb. 11, 1982, Pat. No. 4,430,293.

[51] Int. Cl.³ .................... C07C 29/136; C07C 29/14; C07C 31/20
[52] U.S. Cl. ...................................... 568/861; 568/863
[58] Field of Search ................................ 568/863, 861

[56] References Cited

U.S. PATENT DOCUMENTS

| | | | |
|---|---|---|---|
| 2,004,135 | 6/1935 | Rothrock | 568/861 |
| 2,852,570 | 9/1958 | Conradin et al. | 568/861 |
| 2,965,679 | 12/1960 | Conradin et al. | 568/861 |
| 4,292,451 | 9/1981 | de Berardinis et al. | 568/863 |
| 4,338,472 | 7/1982 | Sirkar | 568/861 |
| 4,404,411 | 9/1983 | Tanikella | 568/861 |

FOREIGN PATENT DOCUMENTS 168666  11/1965  U.S.S.R. ............... 568/863

*Primary Examiner*—J. E. Evans
*Attorney, Agent, or Firm*—Donald L. Johnson; John F. Sieberth; Teresa M. Stanek

[57] ABSTRACT

A process for the production of a lower polyhydric alcohol or a mixture thereof by the hydrogenation and hydrolysis of a carbohydrate. The first stage hydrogenation produces higher polyhydric alcohols, such as sorbitol. In the second stage these higher polyhydric alcohols are selectively converted under the appropriate reaction conditions to lower polyhydric alcohols, such as ethylene glycol and 1,2-propylene glycol, using a sulfide-modified ruthenium catalyst.

12 Claims, No Drawings

TWO STAGE HYDROGENOLYSIS OF CARBOHYDRATE TO GLYCOLS USING SULFIDE MODIFIED RUTHENIUM CATALYST IN SECOND STAGE

This application is a division of application Ser. No. 348,026, filed Feb. 11, 1982, now U.S. Pat. No. 4,430,253.

BACKGROUND

1. Field of the Invention

This invention relates to the catalytic hydrogenation of sugars. This invention further relates to the conversion of carbohydrates to lower polyhydric alcohols by a two stage process. More particularly, this invention relates to the production of lower polyhydric alcohols from sorbitol, mannitol, xylitol and the like, by hydrogenolysis in the presence of a sulfide-modified ruthenium catalyst.

2. Description of the Prior Art

Generally, the prior art methods of producing glycerin and short chain polyols from a starting material of reducible sugar and related carbohydrates require at least two separate stages or steps. Usually in the first stage, the starting material, commonly a hexose, is hydrogenated to produce a polyol corresponding the carbon chain length of the starting material. This polyol is referred to as a higher polyhydric alcohol. In the second stage the higher polyhydric alcohol is cracked, that is, a carbon to carbon linkage in the molecule is broken, and hydrogenated further to produce a polyol product of a shorter carbon chain length than the higher polyhydric alcohol fed into the second step. These polyol products of a shorter chain length are called lower polyhydric alcohols. The two stage operation may be carried out in separate reactors or may be accomplished in a single reactor by varying the reaction conditions. Generally, the first stage is carried out under neutral conditions, at a relatively low temperature, at relatively low pressure, and in the presence of a hydrogenation catalyst. The second stage is carried out in the presence of a catalyst, hydrogen and a base such as calcium oxide, at a relatively high temperature and relatively high pressure. The second stage process is a hydrogenolysis. Hydrogenolysis involves the cracking of a carbon to carbon linkage in a molecule with the simultaneous addition of hydrogen to each of the fragments produced by the cracking.

The term "carbohydrate" as used throughout the specification includes monosaccharides and polysaccharides. This term includes both pure compounds, such as glucose, sucrose and cellulose and mixtures such as corn starch hydrolyzate, which is a hydrolysis product of corn starch containing glucose (dextrose) and oligomers thereof or hydrolyzates of cellulose and hemicellulose containing hexoses and pentoses and oligomers thereof.

The term "polysaccharide" as used in the specification includes those saccharides containing more than one monosaccharide unit. This term also encompasses disaccharides and other saccharides containing a small number of monosaccharide units, which are commonly known as oligosaccharides.

The term "higher polyhydric alcohols" as used in the specification and claims refers to those products that are the result of the first stage hydrogenation of carbohydrates. These compounds include sorbitol, mannitol, xylitol, and the like.

The term "lower polyhydric alcohols" as used in the specification and the claims refers to those products that are the result of the second stage hydrogenolysis of higher polyhydric alcohols. These compounds have a maximum of six carbon atoms and a maximum of three hydroxy groups. Lower polyhydric alcohols include ethylene glycol, propylene glycol, glycerol, erythritol, butane diols, and the like.

A wide variety of catalysts have been proposed for the hydrogenation of monosaccharides such as glucose and fructose to polyhydric alcohols. The catalysts most often used for this purpose are Raney nickel catalysts such as those described in U.S. Pat. No. 2,983,734, and finely divided supported nickel catalysts, such as those disclosed in U.S. Pat. No. 2,749,371.

Supported nickel catalysts described in U.S. Pat. Nos. 3,538,019 and 3,670,035 have high activity for the conversion of both monosaccharides and polysaccharides, including carbohydrate mixtures such as corn starch hydrolyzate with high selectivity to sorbitol when either corn starch hydrolyzate or dextrose is used as the starting material. Carbon, diatomaceous earth, and kieselguhr are disclosed as carriers for the catalyst. This represents a significant improvement over U.S. Pat. No. 2,868,847, since relatively inexpensive corn starch hydrolyzate, or other commercially available carbohydrate mixtures, can be used as the starting material in place of much more expensive pure sugars. Various other nickel catalysts for conversion of carbohydrates to polyhydric alcohols are cited in U.S. Pat. Nos. 3,538,019 and 3,670,035.

The conversion of carbohydrates to polyhydric alcohols using ruthenium on a solid carrier is known. U.S. Pat. No. 2,868,847 discloses the use of ruthenium on an inert support, such as carbon, alumina, silica, or kieselguhr, as a catalyst for the catalytic hydrogenation of saccharides such as dextose, levulose, sucrose, maltose, and lactose. Starting materials include monosaccharides, e.g. dextrose and levulose, and disaccharides, e.g. sucrose, lactose, and maltose. Dextrose was hydrogenated to sorbitol. Sucrose and lactose were hydrolyzed and hydrogenated to hexitols. However, maltose, a disaccharide containing two glucose units, was more easily converted to maltitol, a $C_{12}$ polyol according to the patent.

U.S. Pat. No. 3,055,840 discloses the hydrogenation of various carbonyl compounds, including glucose (which yields sorbitol on hydrogenation), using a promoted ruthenium catalyst on a solid carrier. Various solid carriers, including carbon, silica gel, alumina, kieselguhr, and titanium dioxide, are disclosed.

U.S. Pat. No. 3,963,788 describes and claims a process for the conversion of a carbohydrate to a polyhydric alcohol using a ruthenium-containing zeolite having a silica/alumina mole ratio greater than 3, particularly a ruthenium-containing Y type zeolite, as the catalyst. The ruthenium is present as the free metal on the zeolite which serves as a support. Glucose and corn starch hydrolyzate, both of which yield sorbitol are representative carbohydrates. U.S. Pat. No. 3,963,789 describes and claims a process for conversion of a polysaccharide-containing carbohydrate, such as corn starch hydrolyzate, to a polyhydric alcohol using ruthenium on a crystalline aluminosilicate clay as the catalyst. Both of these applications describe regeneration of the catalyst with a dilute aqueous mineral acid.

U.S. Pat. No. 4,072,628 teaches the regeneration of a supported ruthenium catalyst used for the conversion of carbohydrates to polyhydric alcohols. This is a first stage hydrogenation. The catalyst is contacted with an aqueous solution of a mineral acid, such as sulfuric, hydrochloric or phosphoric acid.

The above-cited references describe a variety of catalytic processes for the conversion of carbohydrates to polyhydric alcohols, however, none describe the use of a sulfide-modified ruthenium catalyst in the second stage hydrogenolysis of polyhydric alcohols, such as sorbitol, to lower polyhydric alcohols. The use of a sulfide-modified catalyst in this second stage allows a greater range of reaction temperatures to be used and a higher product selectivity. The traditional hydrogenation catalyst generally result in a wide range of products. Typical reaction products include methane, methanol, ethanol, ethylene glycol, 1,2-propylene glycol, 1,3-propylene glycol, glycerine, erythritol, xylitol, and the like. Unmodified ruthenium generally produces a large quantity of methane. By contrast, using a sulfide-modified ruthenium catalyst and a base, these large amounts of methane can be eliminated. This provides greater selectivity. The sulfide-modified ruthenium catalyst results in a product mixture comprised largely of ethylene glycol and 1,2-propylene glycol. Under the appropriate reaction conditions, approximately 91% of the product mixture may be composed of these two glycols. These glycols have application in a wide variety of products. Typical uses include polyester fiber intermediates, polyurethane intermediates, plasticizer intermediates and detergents.

SUMMARY OF THE INVENTION

In accordance with the present invention, the conversion of higher polyhydric alcohols, such as sorbitol, to lower polyhydric alcohol can be carried out using a sulfide-modified ruthenium catalyst. A high selectivity for ethylene glycol and 1,2-propylene glycol is achieved.

DESCRIPTION OF THE PREFERRED EMBODIMENTS

The reaction is carried out in two stages. Generally, the two stage operation results in a better conversion to the desired polyhydric alcohol or alcohols with smaller amounts of impurities. The second stage in the two stage operation is generally conducted at a higher temperature than the first stage. The two stage treatment allows for more efficient hydrogenolysis of polysaccharides.

The present invention relates to an improvement in a process for the production of a lower polyhydric alcohol or a mixture thereof which comprises a first stage of contacting an aldose- or ketose-containing carbohydrate with hydrogen in the presence of a first catalyst and under non-basic conditions to obtain a higher polyhydric alcohol or a mixture thereof and a second stage of further contacting said higher polyhydric alcohol or mixture thereof with hydrogen in the presence of a base and a second catalyst. The improvement comprises using a sulfide-modified ruthenium catalyst as the second catalyst.

The carbohydrate starting material can be a monosaccharide or mixture thereof, or a polysaccharide-containing material. The latter term encompasses disaccharides and mixtures thereof, as well as carbohydates comprising both a monosaccharide (or monosaccharides) and a polysaccharide (or polysaccharides). Preferred polysaccaride-containing starting materials are those which are readily hydrolyzable to monosaccharides under dilute acid conditions. These readily hydrolyzable polysaccharide-containing starting materials may be water-soluble, and the polysaccharide content is essentially in the form of lower molecular weight polysaccharides, i.e., oligosaccharides. These starting materials for the present process are known in the art as starting materials for the production of polyhydric alcohols by catalytic hydrogenation in the case of monosaccharides, or hydrolysis and hydrogenation in the case of polysaccharides.

Monosaccharides which can be converted to polyhydric alcohols include glucose, fructose, galactose, mannose, arabinose, ribose and xylose. Mixtures of monosaccharides and, in particular, invert sugar (a mixture glucose and fructose) can also be treated.

Disaccharides which can be converted into polyhydric alcohols include sucrose, maltose, lactose, cellobiose, and mellobiose. Raffinose is a suitable trisaccharide starting materials include starch and starch decomposition products such as dextrin, glucose syrup, cellulose hydrolyzates and starch hydrolyzates, e.g., cornstarch hydrolyzate.

Corn starch hydrolyzate is a particularly preferred starting material in the present process because of its low cost. Other starch hydrolyzates are similar in composition to corn starch hydrolyzate and can also be used with good results. Corn starch hydrolyzate is a product of the hydrolysis of corn starch to glucose. The hydrolyzate as produced contains some impurities, including electrolytes, which might be detrimental in the present process. These impurities can be removed by treatment with a combination of a cation exchange resin and an anion exchange resin. The purified corn starch hydrolyzate, which is used as a starting material for the present process, consists essentially of glucose (D-glucose or dextrose) and polymers thereof (primarily low molecular weight polymers or oligosaccharides, e.g., di-, tri-, and tetrasaccharides) which are composed entirely of glucose units and which, therefore, yield glucose as the only monosaccharide on hydrolysis.

High molecular weight polysaccharides, such as cellulose and insoluble starch (i.e., corn starch) can be used as starting materials but generally require more severe conditions of hydrolysis.

Monosaccharides containing an aldehyde group (e.g., aldoses) are hydrogenated almost exclusively to a single polyhydric alcohol. Glucose, for example, is hydrogenated almost exclusively to sorbitol.

Monosaccharides containing a keto group in the molecule (i.e., ketoses) are hydrogenated to a mixture of two different isomeric polyhydric alcohols. Fructose, for example, has a keto group at the second carbon atom and is hydrogenated to approximately equal amounts of sorbitol and mannitol. Invert sugar, which consists of equimolar quantities of glucose and fructose is hydrogenated to a reaction product containing approximately three moles of sorbitol for each mole of mannitol.

Polysaccharides are hydrolyzed to their basic monosaccharide (or monosaccharides) whose aldehyde or ketone groups are then hydrogenated to hydroxyl groups to produce the desired polyhydric alcohol (or alcohols) of the monosaccharide. Those polysaccharides having free aldehyde or ketone groups in their molecular structure may have these groups hydrogenated at the same time the molecule is hydrolyzed. Polysaccharides composed of different monosaccharide units are hydrolyzed and hydrogenated to the polyhydric alcohols of the respective monosaccharides. When sucrose (whose basic structural monosaccharides are glucose and fructose) is hydrolyzed and hydrogenated, the resulting reaction product is a sorbitol-mannitol mixture in the molar ratio of approximately 3-1. Corn starch hydrolyzate (in which the polysaccharides consist of glucose units) yields sorbitol, with isomers thereof (i.e., mannitol and iditol) present only in small by-products amounts.

The present process is conveniently carried out in an aqueous reaction medium. However, a variety of other solvents may be employed. Non-limiting examples of alternative solvents include ethylene glycol, propylene glycol, monomethyl ether of diethylene glycol, dimethyl ether of diethylene glycol, methyl carbitol, tetrahydrofuran, dibutyl ether, dimethylformamide, sulfolane and alcohols having 1-4 carbon atoms. The solvents may be used alone or in combination with any other solvent including water.

The carbohydrate or carbohydrates to be subjected to the process of this invention may be dissolved in water at the appropriate concentration for the conversion reaction. Concentrations of carbohydrates from about 20% to about 80% by weight are usually employed for the reaction. Carbohydrate concentrations in the range of about 40% to about 70% by weight react particularly smoothly in the reaction and such concentrations are, therefore, the more preferred for this invention. It is not necessary for the carbohydrates to form true solutions with the water, as true suspensions or colloidal suspensions of carbohydrates readily react.

Well-known hydrogenation catalysts are intended for use in the first stage of the reaction. The most common metals include ruthenium, nickel, cobalt and copper. The ruthenium metal may be deposited on some other metal such as nickel, copper, zinc or silver. The ruthenium may also be present as ruthenium on charcoal (carbon). Nickel is frequently used as nickel on carbon, Raney nickel or nickel on kieselguhr. Other typical forms of hydrogenation catalysts include copper on an aluminum oxide support, copper chromite and cobalt on carbon.

The amount of catalyst to be used in the process of this invention may vary over a wide range and will depend upon the particular catalyst, carbohydrate, temperature, and pressure which are employed in the process. Polysaccharides tend to require a higher level of catalysts than the monosaccharides. Catalyst metal concentrations generally range from about 0.1% to about 1.0% based on the weight of carbohydrate. Preferably, the catalyst concentrations range from about 0.2% to about 0.5%.

The temperature, pressure and reaction time used in the conversion of a carbohydrate herein may vary over a wide range. The reaction should be carried out at a temperature high enough to allow the reaction to proceed, yet not so high as to cause degradation of the reactants and products. A temperature range of about 50° to about 200° C. is a useful range in which to operate. In the first stage, a temperature from about 100° C. to about 175° C. is preferred. The most preferred temperature ranges from about 120° C. to about 160° C. The hydrogen pressure should be at least about 50 psig. The pressure range is from about 50 psig to about 3000 psig. Preferably, the pressure ranges from about 100 psig to about 2000 psig. More preferably, the pressure is within the range of 100 psig to about 1000 psig. It is to be understood that higher and lower temperatures and pressures than those described above may be used when deemed necessary or desirable to optimize results.

The time of reaction will depend upon the specific carbohydrate or carbohydrates being acted upon, the specific hydrogenation catalyst used, pressure, temperature and the concentration of the carbohydrate. Generally, the time may be about 15 to about 100 minutes in the first stage hydrogenation. However, some reactions may take longer or shorter periods of time. In any event, the reaction should be continued until the hydrogenation is substantially complete forming higher polyhydric alcohols.

In general, the conversion of polysaccharide-containing materials tends to require higher catalyst levels, higher temperatures and longer reaction times than the hydrogenation of monosaccharides. Pressures used for conversion of both monosaccharides and polysaccharides containing carbohydrates are about the same.

Suitable reaction medium pH values are determined by both the catalyst support and the starting carbohydrate used. The reaction medium should be non-basic. The pH of the reaction medium in the first stage should range from about 2.5 to about 7.0.

Polysaccharide-containing starting materials such as corn starch require a pH not above about 4.5 and preferably not above about 4.0, in order to obtain complete hydrolysis of polysaccharides. An acid, such as sulfuric acid or phosphoric acid, can be added to the first stage reaction medium, either at the outset or during the reaction, e.g., between the first and second stages (the latter is ordinarily preferred), for pH control. Hydrochloric acid can also be used but is harmful to stainless steel equipment.

The reactants may be added to the reaction chamber in any suitable manner or in any suitable order. It is preferred to add the catalyst to the aqueous solution or suspension of the carbohydrate and then add the hydrogen under pressure and commence heating the mixture to the desired temperature.

The reaction is carried out in any suitable type of apparatus which enable intimate contact of the reactants and control of the operating conditions and which is suitable for the high pressures involved. The process may be carried out in batch, semi-continuous, or continuous operation. Batch operation in a conventional autoclave gives excellent results.

Upon completion of the stage one reaction, the catalyst may be removed by filtration or decantation and the reaction mixture may be immediately subjected to the second stage hydrogenolysis. Typical higher polyhydric alcohols obtained in this first stage hydrogenation include sorbitol, mannitol, xylitol, and the like.

The second stage reaction involves the hydrogenolysis of these polyhydric alcohols to desirable lower polyhydric alcohols. Lower polyhydric alcohols obtained in high yield as taught by the present invention include ethylene glycol and 1,2-propylene glycol. According to the present invention, a sulfide-modified ruthenium catalyst is used to obtain this limited range of products.

The ruthenium catalysts intended for use in the present invention are among those well-known in the art. The ruthenium catalyst may be prepared by dissolving a soluble ruthenium compound in a suitable solvent and impregnating the support with the ruthenium/solvent mixture. The supported catalyst is the dried and reduced with hydrogen at elevated temperatures.

Preferably, the ruthenium is in the form of ruthenium halide. More preferably, the ruthenium is ruthenium chloride.

Suitable solvents include water, ethylene glycol, propylene glycol, monomethyl ether of diethylene glycol, dimethyl ether of diethylene glycol, methyl carbitol, tetrahydrofuran, dibutyl ether, dimethylformamide, sulfolane, and alcohols having 1-4 carbon atoms. The solvents may be used alone or in combination with any other solvent. Preferably, the soluble ruthenium compound is dissolved in water.

Suitable supports include charcoal (carbon), titania, alumina, magesia zirconia and the like. The preferred support is carbon. The amount of ruthenium on the support can vary over a wide range. Typically, 0.1-10 weight percent of the supported ruthenium catalyst is ruthenium. Preferably, 0.5-9.0 weight percent of the catalyst is ruthenium. More preferably, 1.0-7.0 weight percent of the catalyst is ruthenium. A carbon supported catalyst can be prepared using $RuCl_3.1-3H_2O$ in distilled water and impregnating a carbon support with the ruthenium water mixture. The catalyst is then stripped of all water until a free-flowing powder is obtained. The solid is packed in the tube of a horizontal tube furnace. A hydrogen flow is started over the catalyst. The temperature is raised from about 25° C. to about 400° C. and held there for about 2 to 16 hours. The catalyst is cooled and stored until ready for use. Supported ruthenium catalysts may also be purchased commercially. Typically, 0.1 weight percent to about 10 weight percent ruthenium on a support is desirable in the present invention.

Various techniques are available to make a sulfide-modified ruthenium catalyst for the stage two hydrogenolysis of higher polyhydric alcohols to lower polyhydric alcohols. The sulfide modification of the ruthenium catalyst can be accomplished either before or after the addition of the supported ruthenium catalyst to the carbohydrate or higher polyhydric alcohol solution.

The carbon supported ruthenium catalyst is obtained commercially or prepared in the manner indicated above. The catalyst is then added directly to the carbohydrate solution. The catalyst may optionally be placed in a solvent prior to this addition. The carbohydrate solution contains 20-80 weight percent of carbohydrate. The carbohydrate solution is hydrogenated at a temperature of from about 50° C. to about 200° C. at about 50 to about 3000 psig of hydrogen to convert the carbohydrate to a higher polyhydric alcohol. Once the autoclave contents are cooled and the autoclave is opened a catalyst promoter is generally added next. The catalyst is then modified by the addition of a sulfide-containing solution in an amount sufficient to provide from about 0.2 to about 5.0 moles of sulfide per mole of ruthenium. The carbohydrate solution is then heated from about 150° C. to about 300° C. for a period sufficient to complete the conversion of the higher polyhydric alcohols to lower polyhydric alcohols. The contents may be cooled and filtered to obtain the desired lower polyhydric alcohol products.

Alternatively, a sulfide modified ruthenium catalyst can be completely prepared prior to the addition of the polyhydric alcohol solution. About 1-5 parts by weight of a soluble ruthenium compound is dissolved in about 20 to about 400 parts of solvent. This ruthenium-containing solution is added to about 10 to about 50 parts of a catalyst support. Then a sulfide-containing solution is added in an amount sufficient to provide from about 0.2 to about 5.0 moles of sulfide per mole of ruthenium. The solvent is vaporized from the catalyst mixture usually until a free-flowing product is obtained. It is contacted with hydrogen at about 300° C. to about 400° C. The hydrogen flow is generally carried out by placing the solid in a tube of a horizontal tube furnace. Once the temperature is raised from about 300° C. to about 400° C., it is typically held there for about 2 to about 16 hours. The catalyst is cooled and stored until ready for use.

Sulfide may be introduced into the reaction system in the form of a convenient salt. It is believed that the sulfide compound selected to modify or poison the ruthenium catalyst should be easy to reduce to enable it to interact with the ruthenium on the surface of the catalyst. Thus, any material capable of giving up sulfur to ruthenium to form a ruthenium sulfide is considered to be a sulfiding material. Non-limiting examples are sodium sulfide, sodium thiosulfate, sodium bisulfite and carbon disulfide. Even gaseous $H_2S$ would be effective. Equally applicable would be an organic material that will decompose to sulfide ion moieties. It is speculated that these readily ionizable compounds dissociate and the sulfide ions are then able to interact with the ruthenium on the surface of the catalyst. Sodium sulfate is not a suitable poison perhaps because it is a relatively stable compound and not likely to disproportionate to any appreciable extent.

The modified ruthenium can contain sulfide ions in proportions dictated by the conditions of the reaction and the specific ratios of the products desired. These sulfide ion proportions relative to ruthenium may vary from about 0.2 mole to about 5.0 moles of sulfide per mole of ruthenium. Preferably, there are from about 0.5 to about 2.0 sulfide ions per ruthenium molecule. More preferably, there are about 0.5 to about 1.0 moles of sulfide ion per mole of ruthenium. If there are less than 0.5 sulfide ions per ruthenium atom a large amount of methane results. A ratio of 0.5 to 1.0 sulfide ion per ruthenium atom is optimum for ethylene and propylene glycol products. If the ratio of sulfide ion to ruthenium is greater than 2, the product distribution changes dramatically and alcohols and paraffins are formed. Even some hexane is produced from glucose.

The sulfide modified ruthenium catalyst may be recycled. Some activity may be lost after the first reaction. Generally, no change in activity results after further use.

The amount of ruthenium present on the support is about 0.1-10 weight percent of the catalyst composition. Preferably, 0.5-9.0 weight percent of the catalyst is ruthenium. More preferably, 1.0-7.0 weight percent of the catalyst is ruthenium.

A promoter is beneficial in the second stage hydrogenolysis. This promoter component is a base. Useful basic materials include alkali metal hydroxides and basic salts, alkaline earth metal oxides, hydroxides and basic salts, and quaternary ammonium salts. Non-limiting examples are calcium oxide, sodium hydroxide, sodium carbonate or any practical combination of alkali or alkaline earth salts that will induce basicity into the hydrogenolysis medium. Also included are the tetraalkyl quaternary ammonium salts. The preferred base is calcium oxide.

The amount of base used depends on the base selected First, an amount of base is added to bring the reaction up to neutrality. Then an additional amount of base is added to obtain the desired ratio of base to higher polyhydric alcohol. The base is preferably within the range of about 0.025 gram to about 0.1 gram of base per gram of higher polyhydric alcohol. More preferably, there is about 0.06 gram to about 0.1 gram of base per gram of higher polyhydric alcohol.

It is important to maintain the pH range during the second stage of the reaction. The pH is generally in the range of 8.0 to 13.0. Preferably, the pH is in the range of 9.0 to 11.0. The co-catalyst or base maintains the pH within the desired range. Maintaining the pH within this range is important to achieve product selectivity.

The second stage hydrogenolysis is conveniently carried out in an aqueous reaction medium. However, a variety of other solvents may be employed. Non-limiting examples of alternative solvents include ethylene glycol, propylene glycol, monomethyl ether of diethylene glycol, dimethyl ether of diethylene glycol, methyl carbitol, tetrahydrofuran, dibutyl ether, dimethylformamide, sulfolane and alcohols having 1-4 carbon atoms. The solvents may be used alone or in combination with any other solvent including water.

The reaction conditions of the second stage hydrogenolysis will depend on the extent of the ruthenium modification and the products desired. If a high yield of glycerine, rather than ethylene glycol and propylene glycol, is desired, then milder reaction conditions can be employed.

The reaction should be carried out at a temperature high enough to allow the reaction to proceed, yet not so high as to cause degradation of the reactants and products. The temperature in this second stage hydrogenation is within the range of about 150° C. to about 300° C. Preferably, the temperature is within the range of about 190° C. to about 250° C. More preferably the temperature is within the range of about 220° C. to about 250° C.

The hydrogen pressure can vary over a wide range, a preferred range is about 500 psig to about 5000 psig. More preferably, the pressure is within the range of about 1000 psig to about 5000 psig. Most preferably, the pressure is within the range of about 2000 psig to about 3000 psig.

It is to be understood that higher and lower pressures and temperatures than those described above may be used when deemed necessary or desirable.

The time of reaction will directly depend on the other reaction conditions. The hydrogenolysis should be conducted for the time required to convert the higher polyhydric alcohol to lower polyhydric alcohol. Generally, the stage two hydrogenolysis requires about 15 minutes to about 100 minutes. However, some reactions may take longer or shorter periods of time. In any event, the reaction should be continued until the hydrogenolysis is substantially complete.

The reactants may be added to the reaction vessel in any suitable manner or in any suitable order. It is preferred to add the catalyst to the aqueous solution or suspension of the polyhydric alcohol, add the base and then add the hydrogen under pressure and commence heating the mixture to the desired temperature.

The reaction is carried out in any suitable type of apparatus which enables intimate contact of the reactants and control of the operating conditions and which is suitable for the higher pressures involved. The process may be carried out in batch, semi-continuous, or continuous operation.

Upon completion of the second stage reaction, the catalyst is removed by filtration or decantation and the lower polyhydric alcohols are separated from the filtrate by any suitable means, such as solvent extraction or distillation.

The products formed upon completion of the second stage hydrogenolysis are predominately ethylene glycol and 1,2-propylene glycol. The yield of this group of products can be as high as 91%. However, lower amounts may occur depending on the exact starting material and specific reaction conditions selected.

In order that those skilled in the art may better understand how the present invention may be practiced, the following examples are given. These examples are set forth solely for the purpose of illustration and any specific enumeration of details contained therein should not be interpreted as expressing limitations with this invention.

EXAMPLE 1

This example demonstrates the preparation of a ruthenium catalyst on a carbon support.

2.9 g of $RuCl_3 \cdot 1\text{-}3H_2O$ (Alfa ® No. 64103) was dissolved in 75 ml of distilled water. 25 g of Calgon ® Activated Carbon (type C-pulverized) was added. The mixture was shaken well and placed in a 500 ml round-bottom flask and all water evaporated until a free-flowing powder was obtained. The solid was packed in the tube of a horizontal tube furnace (with glass-wool plugs to hold the catalyst in a plug in the tube). Hydrogen flow was started over the catalyst and the temperature was raised to 400° C. and held there for 16 hours and then cooled and stored in a jar.

EXAMPLE 2

This example demonstrates the preparation of a carbon supported ruthenium catalyst modified with sulfide ions prior to the addition of the higher polyhydric alcohol solution.

To a 500 ml round bottom flask was added 25 g of Calgon ® Activated Carbon (type BL, pulverized) and a solution of 3.0 g of $RuCl_3$ [Alfa ® ruthenium (III) chloride (43.04% Ru; 3.8% $H_2O$)] in 70 grams of water. The suspension was shaken well for 20 minutes and then a solution of 4.5 ml of 50% $Na_2S \cdot 9H_2O$ in water was added. The mixture was again shaken for 15 minutes and then the flask was stipped free of water on a Rinco ® evaporator (steam bath heat). After a free flowing powder was obtained, the solid was then added to a tube which was placed in a horizontal furnace. Hydrogen flow was started through the catalyst bed and the catalyst was reduced at 400° C. for 16 hours while hydrogen flow was continued. The catalyst was cooled under hydrogen and then transferred to a nitrogen flushed jar for storage until ready for use.

EXAMPLE 3

This example demonstrates the preparation of a ruthenium catalyst on a carbon support that is modified after the addition of the polyhydric alcohol solution.

A solution of 40 g Dextrose (Baker anhydrous glucose) and 5 g of 5% ruthenium or carbon by Alpha ® Products was charged to a 300 ml stirred Magne-Drive autoclave. The autoclave was pressurized with hydrogen and vented. This was repeated several times and then the pressure was set at about 1000 psi of hydrogen. The temperature was raised (while stirring) to about 115° C. Hydrogen uptake started before the reaction temperature had been reached and stopped in less than 15 minutes (total pressure drop was 450 psi). The autoclave and contents were cooled and the autoclave was opened and 3 g of calcium oxide and 1.0 ml of 50% aqueous Na₂S.9H₂O was added (equivalent to 1 atom of sulfur per 1 atom of ruthenium contained on the catalyst forming the required sulfide-modified ruthenium catalyst. The autoclave was pressured as above and the contents were then stirred and heated to 220° C. and stirred at that temperature for 4 hours. The contents were cooled and the gases vented to about 200 psig and a gas sample was taken. Residual gas was vented and the product was discharged. The product contained ethylene glycol, propylene glycol, and minor amounts of glycerine, erythritol, xylitol and sorbitol.

EXAMPLES 4–9

These examples demonstrate the conversion of sorbitol to lower polyhydric alcohols using different amounts of Na₂S to modify the 5% ruthenium catalyst on a carbon support. The experiments were carried out using the following general procedure.

A 300 ml stirred Magne-Drive autoclave was charged with a solution of 40 g of sorbitol in 80 g water. Then, 2 g of calcium oxide, 5 g of 5% ruthenium on carbon and from 0–1.0 mole of Na₂S per mole of ruthenium was added. The autoclave was sealed and pressured with hydrogen, then vented. This was repeated 3 times. Hydrogen was charged to 2400 psig and the reactants were heated. The contents were held at this temperature for 4 hours. The pressure rose to about 3300 psig and then dropped to about 2000 psig. The contents were cooled and a gas sample was taken and then the autoclave was vented. The product was discharged, weighed and filtered to remove catalyst. The clear solution was analyzed by vapor phase chromatography on a Porapak Q column (10′ long) using pyridine as the internal standard. The amounts of lower (methanol, ethanol, etc.) alcohols and ethylene and propylene glycol were determined. Glycerol, polyols and sorbitol were analyzed by high pressure liquid chromatography. The analytical results were calculated as carbon mole percent yields. The results are given in the following table.

TABLE I

| Example | Temp (%) | Sulfide Compound | Moles of Sulfide per Moles of Ruthenium | Conversion (% of Sorbitol) |
| --- | --- | --- | --- | --- |
| 4 | 190 | Na₂S | 0 | 98+ |
| 5 | 190 | Na₂S | 0.2 | 93 |
| 6 | 190 | Na₂S | 0.5 | 89 |
| 7 | 190 | Na₂S | 1.0 | 79 |
| 8 | 225 | Na₂S | 1.0 | 94 |
| 9 | 250 | Na₂S | 1.0 | 98+ |

| | | | | Product Distribution (Carbon %) | | | | |
| --- | --- | --- | --- | --- | --- | --- | --- | --- |
| Example | Methane | Methanol | Ethanol | Ethylene Glycol | Propylene Glycol | Glycerol | Erythritol | Xylitol | Other |
| 4 | 25 | 1.3 | .6 | 12 | 27 | 11.4 | 3 | 3 | — |
| 5 | 4 | .3 | — | 20 | 53 | 6.4 | 3 | 6 | .3 |
| 6 | 3 | .6 | — | 20 | 47 | 19.5 | 3 | 11.9 | .4 |
| 7 | .06 | .6 | — | 19.2 | 48.6 | 12.8 | 3 | 4 | .4 |
| 8 | .05 | .5 | — | 25.4 | 59.5 | 11.1 | 3 | 3 | .7 |
| 9 | .05 | 1.2 | — | 26.2 | 64.6 | 3.1 | 3 | 3 | — |

As demonstrated in Example 9, under the listed reaction conditions, the sorbitol conversion was greater than 98+% and produced a 91% yield of ethylene and propylene glycol. The glycerol yield was only 3% and the methane yield was insignificant. Thus, the process is highly selective.

EXAMPLES 10–12

These examples show both the stage one and stage two conversion of a glucose solution to lower polyhydric alcohols.

A typical run was made as follows: A 300 ml stirred Magne-Drive autoclave was charged with a solution of 40 g Dextrose (Baker anhydrous glucose), 80 gm water and 5 g of 5% of ruthenium on carbon. The autoclave was pressured with hydrogen and vented. This was repeated several times and the pressure was set at about 1000 psig of hydrogen. The temperature was raised (while stirring) to about 115° C. Hydrogen uptake started before the reaction temperature had been reached and stopped in less than 15 minutes (total pressure drop was 450 psig). The autoclave and contents were cooled and the autoclave was vented and opened. Then 3 g of calcium oxide and 1.0 ml of 50% aqueous Na₂S.9H₂O was added (equivalent to 1 sulfur atom per ruthenium atom contained on the catalyst) and the autoclave was pressurized as above and the contents were then stirred and heated to 220° C. for 4 hours. The contents were then cooled and the gases were vented to about 200 psig and a gas sample was taken. Residual gas was vented and the product was discharged and a small sample was filtered to remove the catalyst. The liquid was analyzed for alcohols and lower polyols. Higher polyols were analyzed by high pressure liquid chromatography. The analytical results were calculated as carbon mole percent yields.

TABLE II

| Example | Catalyst | Sulfide Compound | Moles of Sulfide per Moles of Ruthenium | Conversion (% of Glucose) |
| --- | --- | --- | --- | --- |
| 10 | 5 gm 5% Ru/C | Na₂S | 0.2 | 97 |
| 11 | 5 gm 5% Ru/C | Na₂S | 0.5 | 97 |
| 12 | 5 gm 5% Ru/C | Na₂S | 1.0 | 97 |

Product Distribution (Carbon %)
Ethylene   Propylene

TABLE II-continued

| Example | Methane | Methanol | Ethanol | Glycol | Glycol | Glycerol | Erythritol | Xylitol |
|---|---|---|---|---|---|---|---|---|
| 10 | 9 | 2 | — | 14 | 39 | 4 | 1 | 1 |
| 11 | .004 | 2 | — | 20 | 45 | 7 | 1 | 1 |
| 12 | .03 | — | — | 21.9 | 46 | 7 | 2 | 2 |

EXAMPLES 13–18

These different sulfide compounds were tested to determine their efficiency as modifying agents in the conversion of sorbitol to lower polyhydric alcohols.

Typical hydrogenolysis was done as follows: The 300 ml Magna Drive autoclave was charged with 40 g sorbitol, 80 g water, 3 g calcium oxide, 5 g of 5% ruthenium on carbon and the selected sulfide compound. The autoclave was sealed and pressured with 2500 psig of hydrogen. Stirring was started and the autoclave contents were heated to 250° C. and held there for four hours. At the end of the 4 hour period, the autoclave contents were cooled and the gas was vented to about 200 psig and a gas sample was taken. Then the residual gas was vented and the contents of the autoclave were discharged and the product was filtered to remove suspended catalyst.

The gas was analyzed by vapor phase chromatography. The liquid was analyzed for glycerol, erythritol, xylitol, sorbitol, and the like by high pressure liquid chromatography. The results from the three analyses were used to calculate conversions and carbon mole percent yield of all products. Results are shown in Table III.

Table III demonstrates that $Na_2S$ and $Na_2S_2O_3$ are approximately equivalent in effect. On the other hand, $Na_2SO_4$ appears to be inert comparable reaction conditions. Methane and carbon monoxide are the major products.

TABLE III

| Example | Catalyst | Sulfide Compound | Moles of Sulfide per Moles of Ruthenium | Conversion (% of Sorbitol) |
|---|---|---|---|---|
| 13 | 5 gm 5% Ru/C | $Na_2S$ | 1.2 | 100 |
| 14 | 5 gm 5% Ru/C | $Na_2S$ | 4.0 | 100 |
| 15 | 5 gm 5% Ru/C | $Na_2S$ | 0.3 | 100 |
| 16 | 5 gm 5% Ru/C | $Na_2S_2O_3$ | 5.0 | 100 |
| 17 | 5 gm 5% Ru/C | $Na_2SO_4$ | 3.0 | 100 |
| 18 | 5 gm 5% Ru/C | — | — | 100 |

| | Product Distribution (Carbon %) | | | | | | | |
|---|---|---|---|---|---|---|---|---|
| Example | Methane | Methanol | Ethanol | Ethylene Glycol | Propylene Glycol | Glycerol | Erythritol | Xylitol |
| 13 | trace | 2 | 2 | 26 | 40 | 3 | — | — |
| 14 | 0.4 | 2 | 14 | 4 | 23 | 4 | — | — |
| 15 | 2.0 | 3 | 1 | 29 | 46 | — | 2 | — |
| 16 | 0.7 | 1 | 16 | 4 | 12 | — | — | — |
| 17 | 47 | — | — | — | — | 3 | — | — |
| 18 | 77 | — | — | — | — | — | — | — |

We claim:

1. In a process for the production of a lower polyhydric alcohol or a mixture thereof by the hydrogenation and hydrogenolysis of a carbohydrate, said process comprising a first stage of contacting an aldose- or ketose-containing carbohydrate with hydrogen in the presence of a first catalyst and under non-basic reaction conditions to obtain a higher polyhydric alcohol or a mixture thereof and a second stage of further contacting said higher polyhydric alcohol or mixture thereof with hydrogen in the presence of a base and a second catalyst, the improvement wherein said second catalyst is sulfide-modified ruthenium, whereby said higher polyhydric alcohol is selectively converted in high yield to a mixture comprising a substantial amount of ethylene glycol and propylene glycol.

2. A process, as recited in claim 1, wherein said carbohydrate is in an aqueous solution.

3. A process, as recited in claim 2, wherein the ratio of sulfide ions to ruthenium is in the range of about 0.2 to about 5.0 moles of sulfide ions per mole of ruthenium.

4. A process, as recited in claim 3, wherein said ratio of sulfide ions to ruthenium is in the range of about 0.5–1.0 moles of sulfide ions per mole of ruthenium.

5. A process, as recited in claim 4, wherein said first stage is carried out at a temperature in the range of about 50° C. to about 200° C. and said second stage is carried out at a temperature of about 150° C. to about 300° C.

6. A process, as recited in claim 5, in which said second stage is carried out at a temperature in the range of about 190°–250° C. and under a hydrogen pressure of about 500 to about 5000 psig.

7. A process, as recited in claim 6, wherein said higher polyhydric alcohol is sorbitol.

8. A process, as recited in claim 7, wherein said carbohydrate is corn starch hydrolyzate.

9. A process, as recited in claim 7, wherein said carbohydrate is glucose.

10. A process, as recited in claim 7, wherein said base is selected from the group consisting of alkali metal hydroxides and basic salts; alkaline earth metal oxides, hydroxides, and basic salts and quaternary ammonium salts.

11. A process, as recited in claim 10, wherein said base is selected from the group consisting of calcium oxide, sodium carbonate and sodium hydroxide.

12. A process, as recited in claim 11, wherein said base is calcium oxide.

* * * * *